(12) United States Patent
Picht et al.

(10) Patent No.: US 8,326,396 B2
(45) Date of Patent: Dec. 4, 2012

(54) DRY ELECTRODE FOR DETECTING EEG SIGNALS AND ATTACHING DEVICE FOR HOLDING THE DRY ELECTRODE

(75) Inventors: Bernd Picht, Germering (DE);
Alexander Svojanovsky, Gilching (DE)

(73) Assignee: Brain Products GmbH, Gilching (DE)

( * ) Notice: Subject to any disclaimer, the term of this patent is extended or adjusted under 35 U.S.C. 154(b) by 314 days.

(21) Appl. No.: 12/730,721

(22) Filed: Mar. 24, 2010

(65) Prior Publication Data
US 2011/0237923 A1 Sep. 29, 2011

(51) Int. Cl.
*A61B 5/0478* (2006.01)
(52) U.S. Cl. .......... 600/383; 600/390; 600/544
(58) Field of Classification Search .......... 600/383, 600/390, 544
See application file for complete search history.

(56) References Cited

U.S. PATENT DOCUMENTS

| | | | | |
|---|---|---|---|---|
| 2,409,033 A | * | 10/1946 | Garceau | 600/544 |
| 2,426,958 A | | 9/1947 | Ulett, Jr. et al. | |
| 2,549,836 A | * | 4/1951 | McIntyre et al. | 600/383 |
| 3,490,439 A | * | 1/1970 | Rolston | 600/383 |
| 3,659,614 A | * | 5/1972 | Jankelson | 607/139 |
| 4,967,038 A | | 10/1990 | Gevins et al. | |
| 2008/0027345 A1 | | 1/2008 | Kumada et al. | |

FOREIGN PATENT DOCUMENTS

| | | |
|---|---|---|
| EP | 1767147 A1 | 3/2007 |
| WO | 2006096135 A1 | 9/2006 |
| WO | 2008/067839 A1 | 6/2008 |

OTHER PUBLICATIONS

European Search Report dated Sep. 3, 2010.

* cited by examiner

*Primary Examiner* — Lee S Cohen
(74) *Attorney, Agent, or Firm* — Laurence A. Greenberg; Werner H Stemer; Ralph E. Locher

(57) ABSTRACT

An electrode for detecting EEG signals comprises a body comprising a fixture on a first end of the body, and a sensor detachably held by the fixture, wherein the body has an external thread in a portion of the body extending from the first end of the body towards a second end of the body, and the sensor has a brush-like shape with pins protruding off the body. The electrode may be held by an attaching device for holding electrodes for detecting EEG signals, the attaching device comprising a strap including a plurality of holes for accommodating electrodes and a rotary closure connecting a first end of the strap and a second end of the strap.

8 Claims, 3 Drawing Sheets

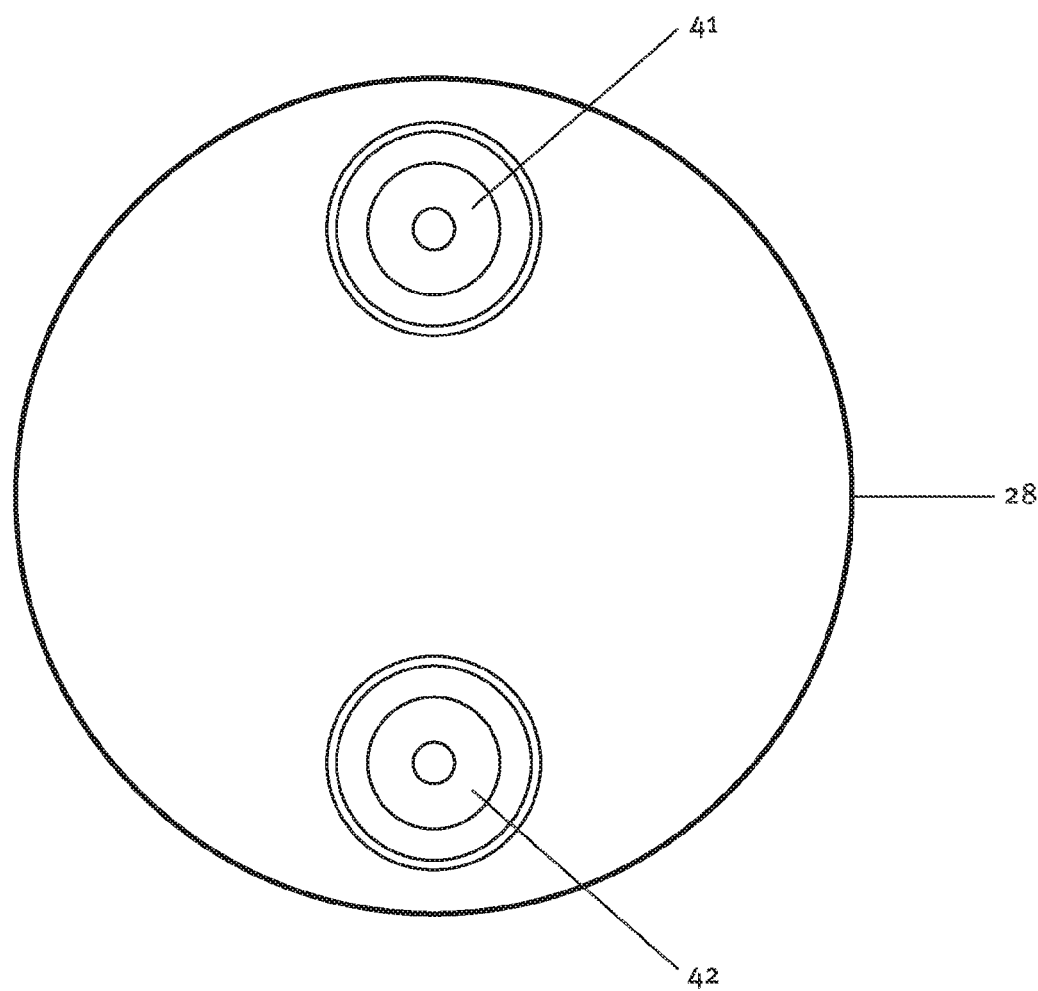

DRY ELECTRODE FOR DETECTING EEG SIGNALS AND ATTACHING DEVICE FOR HOLDING THE DRY ELECTRODE

BACKGROUND OF THE INVENTION

Field of the Invention

The present invention relates to an electrode for detecting EEG signals and an attaching device for holding the electrode which allow contacting the scalp without a conductive gel between the scalp and the electrode.

In order to provide contact between an electrode used for measuring EEG (Electro-Encephalography) signals and the scalp, usually a conductive gel is applied between the skin and the electrode.

However, applying the gel is cumbersome and dry electrodes are aimed for which do not require a conductive gel.

SUMMARY OF THE INVENTION

In particular, the present invention aims at providing a dry electrode for detecting EEG signals and an attaching device for holding the dry electrode which serve to ensure contact between the dry electrode and the scalp through the scalp hair.

Other features which are considered as characteristic for the invention are set forth in the appended claims.

Although the invention is illustrated and described herein as embodied in a dry electrode for detecting EEG signals and attaching device for holding the dry electrode, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 shows a first surface of the rotary closure of the attaching device, according to an embodiment of the invention.

DETAILED DESCRIPTION OF THE INVENTION

Figure 1:
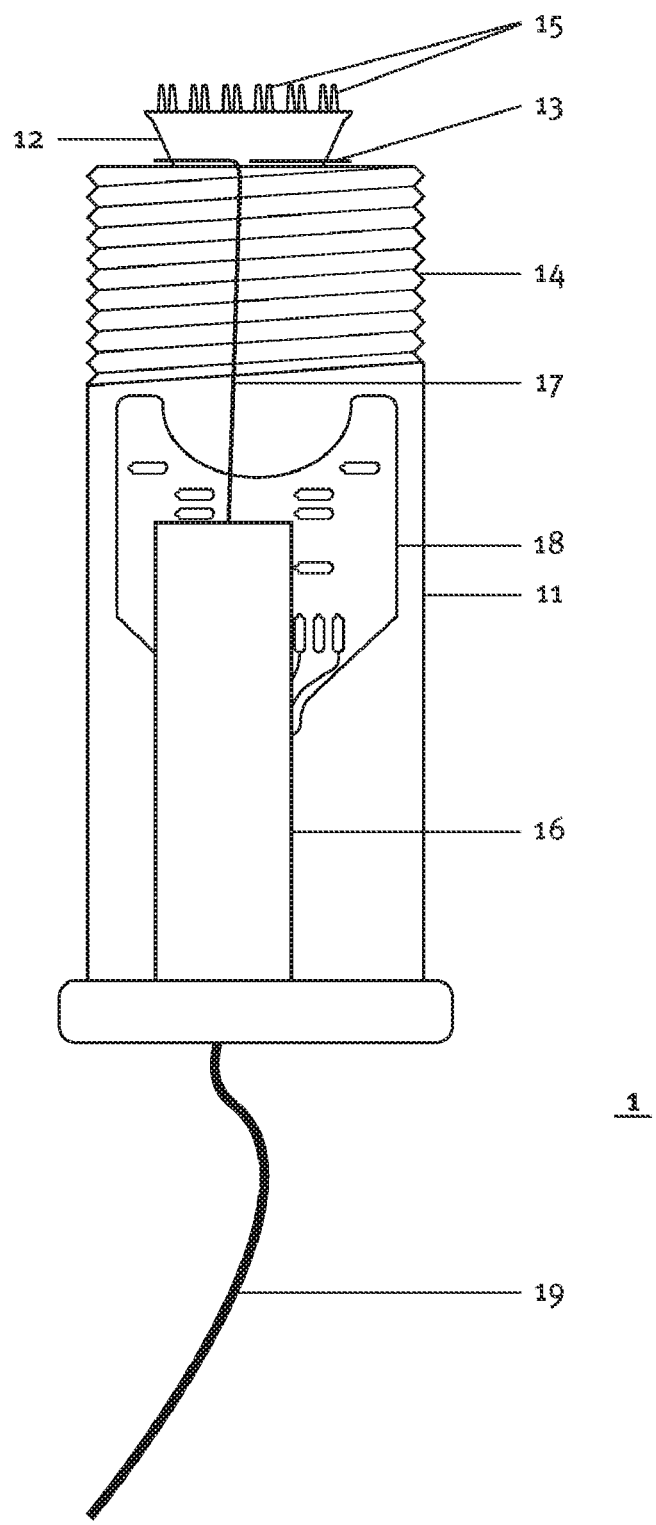
FIG. 1 shows a dry electrode according to an embodiment of the invention.

Referring to FIG. 1 showing an embodiment of the invention, an electrode 1 for detecting EEG signals is shown which comprises a body 11 and a sensor 12. The sensor 12 is detachably held by a fixture 13 of the body 11. The fixture 13 is provided on a first end of the body 11, which is on the side of the scalp when the electrode 1 is attached for detecting EEG signals. In other words, the fixture 13 is formed on a plane of the body 11, which faces the scalp when the electrode 1 is attached for detecting EEG signals. When detecting EEG signals, the sensor 12 is in contact with the scalp and senses an electrical potential at its place on the scalp.

The body 11 may be of cylindrical shape and has an external thread 14 in a portion of the body 11 extending from the first end of the body 11 towards a second end of the body 11, which is off the scalp when the electrode 1 is attached for detecting EEG signals. The external thread 14 may be provided in the first third of the body 11 with respect to a direction from the first end to the second end of the body 11. The external thread 14 serves to attach or fix the electrode 1 in a hole of a strap of an attaching device to be described later, and to adjust the distance between the sensor 12 and the scalp.

The sensor 12 has a brush-like shape with pins 15 protruding off the body 11 and towards the scalp through the scalp hair when the electrode 1 is attached for detecting EEG signals. The sensor 12 is made of Ag, AgCl, Au, Sn or any other conductive material including conductive polymer.

The fixture 13 may be a clip into which the sensor 12 can be clicked and from which the sensor 12 can be detached. This arrangement allows an exchange of the sensor in order to replace the sensor, clean the sensor, etc.

According to an embodiment of the invention, the body 11 may include a vibration element 16 and a connector 17 which transfers a vibration of the vibration element 16 to the sensor 12. The connector 17 may be a rod or the like which is clamped between the vibration element 16 and the sensor 12. By means of the vibration, the sensor 12, in particular the pins 15 of the sensor 12, is/are moved through hair of the scalp, when the electrode 1 is attached for detecting EEG signals. The vibration element 16 may be attached to the second end of the body 11 and may extend in the body 11 towards the first end of the body 11, as shown in FIG. 1. The vibration element 16 may comprise an element including a vibration motor, such as an element as e.g. used in cell phones.

It is to be noted that the vibration element 16 may be arranged at any position in the electrode 1 as long as the vibration of the vibration element can be transferred to the sensor 12 to cause the sensor 12 to vibrate through the scalp hair. The vibration element may also be used as a feedback instrument allowing an inference on an electrical potential sensed by the sensor 12.

The body 11 includes a circuit board 18 which is casted watertight and comprises circuitry for impedance conversion of an electrical potential sensed by the sensor 12 and input to the circuitry and for impedance display. The impedance display may be arranged by LEDs of different colors.

The electrode 1 has a lead 19 which emanates from the second end of the body 11 and receives from the circuit board 18 a signal representing the electrical potential sensed by the sensor 12 and impedance converted by the circuitry of the circuit board 18 and outputs the signal from the electrode 19 for further processing of the signal. The lead 19 may also be used for transferring power to the circuit board 18 and the vibration element 16.

Figure 2:
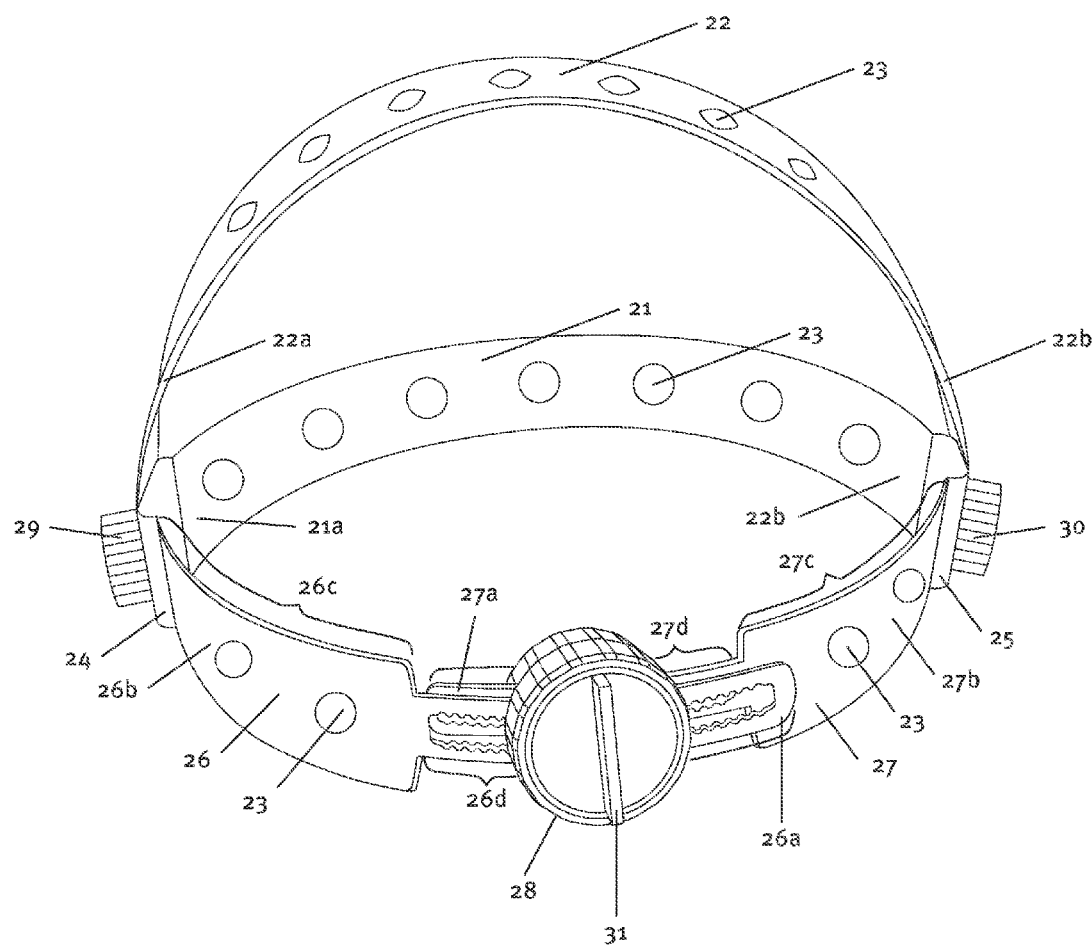
FIG. 2 shows an attaching device for holding dry electrodes according to an embodiment of the invention.

FIG. 2 shows an embodiment of an attaching device 2 for holding electrodes for detecting EEG signals, such as the electrode 1 shown in FIG. 1. When used for detecting EEG signals, the attaching device 2 is placed on a head. According to an embodiment of the invention, the attaching device 2 comprises a first strap 21 including a plurality of holes 23 for accommodating electrodes. As shown in FIG. 2, the attaching device 2 may further comprise a second strap 22 including a plurality of holes 23 for accommodating electrodes. A first joint 24 connects a first end 21a of the first strap 21 and a first end 22a of the second strap 22, and a second joint 25 connects a second end 21b of the first strap 21 and a second end 22b of the second strap 22. The second joint 25 is disposed opposite to the first joint 24.

It is to be noted that the attaching device 2 may comprise several second straps 22 in order to provide for further electrode positions. In case of several second straps 22, first ends 22a of the second straps are connected to the first joint 24, and second ends 22b of the second straps 22 are connected to the second joint 25.

The attaching device 2 further includes a third strap 26, a fourth strap 27 and a rotary closure 28 which connects a first end 26a of the third strap 26 and a first end 27a of the fourth strap 27. A second end 26b of the third strap 26 is connected to the first joint 24 and a second end 27b of the fourth strap 27 is connected to the second joint 25. As shown in FIG. 2, the first, third and fourth straps may be connected to form a ring, and, if present, the second strap may be connected to form an arc over the ring. In case of several second straps 22, these may also be connected to from an arc over the ring.

The third and fourth straps 26, 27 may also include holes 23 for accommodating electrodes in a portion 26c, 27c extending from the second end 26b, 27b towards the first end 26a, 27a, as shown in FIG. 2.

Into the holes 23 electrodes such as the electrode 1 may be placed/screwed so that different lead positions are possible.

According to an embodiment of the invention, the first and second joints 24, 25 may comprise fixing screws 29, 30 allowing fixation and change of the first to fourth straps 21, 22, 26 and 27 in order to adjust the attaching device to different head sizes. Straps of different lengths may be used for the first to fourth straps in order to pattern the form of a head. The first ends 21a, 22a of the first and second straps 21, 22 and the second end 26b of the third strap 26 are inserted into the joint 24 and fixed by the fixing screw 29, and the second ends 21b, 22b of the first and second straps 21, 22 and the second end 27b of the fourth strap 27 are inserted into the joint 25 and fixed by the fixing screw 30, allowing nearly free positioning of the first and second straps and, thus, of electrodes on a head which are inserted into the holes 23.

According to an embodiment of the invention in which the attaching device 2 does not include any second straps 22, the first and second joints 24, 25 and the fixing screws 29, 30 may be omitted, and the first, third and fourth straps may be formed as one strap.

At least one of the first to fourth straps 21, 22, 26, 27 may be made of flexible and/or stretchable material in order to improve adjustment of the attaching device 2 to different head sizes. The first to fourth straps 21, 22, 26 and 27 may be made of polyurethane (PUR).

The third strap 26 and the fourth strap 27 each have a portion 26d, 27d which extends from the first end 26a, 27a towards the second end 26b, 27b and is formed as a rack-like closure aid. The rotary closure 28 includes an actuator (not shown) cogging the rack-like closure aid and an operating element 31 at a second surface of the rotary closure 28, which connects to the actuator, so that a ring formed by the third and fourth straps 26, 27 and the first strap 21 narrows or widens when the operating element 31 is operated by a user of the attaching device 2. That is, when the attaching device 2 is placed on a head, by rotating the operating element 31 the first strap 21 and the third and fourth straps 26, 27 are fastened on the head or released depending on the rotation direction. Thus, contact pressure of electrodes, in particular of the pins 15 of electrode 1, inserted into the holes 23 can be ensured.

The rack-like closure aid may be a flexible rack, preferably having two rows of teeth placed inside and facing each other as shown in FIG. 2, and the actuator may by a rack-wheel.

According to an embodiment of the invention in which the attaching device does not include any second straps 22, the attaching device comprises a strap including a plurality of holes for accommodating electrodes, e.g. the first, third and fourth straps shown in FIG. 2 formed as one strap. The attaching device further comprises a rotary closure, such as the rotary closure 28, connecting a first end of the strap and a second end of the strap. The first end of the strap may be similar to the first end of the third strap 26 shown in FIG. 2, and the second end of the strap may be similar to the first end of the fourth strap 27 shown in FIG. 2. The strap may have a first portion at the first end and a second portion at the second end, wherein the first and second portions are formed as a rack-like closure aid. The first portion may be similar to the portion 26d of the third strap shown in FIG. 2, and the second portion may be similar to the portion 27d of the fourth strap shown in FIG. 2. The strap may be made of flexible material.

The attaching device with the above arrangements can be easily fit and adjusted to each head shape. Once the attaching device has been fit and adjusted to a person's head, re-fitting the attaching device to the person's head can be done even quicker.

Referring to FIG. 3 showing a plan view of a first surface of the rotary closure 28, the rotary closure 28 includes a reference electrode 41 and a ground electrode 42 which are arranged centrally and on top of each other on the first surface of the rotary closure 28. The reference electrode 41 and the ground electrode 42 are in contact with a forehead when the attaching device 2 is placed on a head and are positioned substantially centrally and on top of each other on a center line of the head. When the attaching device 2 is placed on the head it is substantially symmetric to a plane passing through the center line of the head and bisecting the head.

The first surface of the rotary closure 28 shown in FIG. 3 is opposite to the second surface of the rotary closure 28 shown in FIG. 2.

The reference electrode 41 and the ground electrode 42 may be designed as cup electrodes or pads.

The rotary closure 28 may have a round shape as shown in FIG. 3, but is not limited thereto.

It is to be understood that the above description is illustrative of the invention and is not to be construed as limiting the invention. Various modifications and applications may occur to those skilled in the art without departing from the true spirit and scope of the invention as defined by the appended claims.

The invention claimed is:

1. An attaching device for holding electrodes for detecting EEG signals, the attaching device comprising:
    a strap including a plurality of holes for accommodating electrodes; and
    a rotary closure connecting a first end of the strap and a second end of the strap; and
    wherein the rotary closure includes a reference electrode and a ground electrode which are arranged centrally and on top of each other on a first surface of the rotary closure, wherein the reference electrode and the ground electrode are in contact with a forehead when the attaching device is placed on a head and are positioned substantially centrally and on top of each other on a center line of the head.

2. The attaching device of claim 1, wherein the strap has a first portion at the first end and a second portion at the second end, wherein the first and second portions are formed as a rack-like closure aid, and the rotary closure includes an actuator cogging the rack-like closure aid and an operating element at a second surface of the rotary closure, which connects to the actuator so that a ring formed by the strap narrows or widens when the operating element is operated.

3. The attaching device of claim 1, wherein the strap is made of flexible material.

4. An attaching device for holding electrodes for detecting EEG signals, the attaching device comprising:

a first strap and at least one second strap each including a plurality of holes for accommodating electrodes;

a first joint connecting a first end of the first strap and a first end of the at least one second strap, and a second joint connecting a second end of the first strap and a second end of the at least one second strap;

a third strap and a fourth strap; and a rotary closure connecting a first end of the third strap and a first end of the fourth strap, the rotary closure including a reference electrode and a ground electrode arranged centrally and on top of each other on a first surface of the rotary closure;

wherein a second end of the third strap is connected to the first joint and a second end of the fourth strap is connected to the second joint; and wherein the reference electrode and the ground electrode are in contact with a forehead when the attaching device is placed on a head and are positioned substantially centrally and on top of each other on a center line of the head.

5. The attaching device of claim 4, wherein the third strap and the fourth strap each have a portion which extends from the first end towards the second end and is formed as a rack-like closure aid, and the rotary closure includes an actuator cogging the rack-like closure aid and an operating element at a second surface of the rotary closure, which connects to the actuator so that a ring formed by the third and fourth straps and the first strap narrows or widens when the operating element is operated.

6. The attaching device of claim 4, wherein the first and second joints comprise fixing screws.

7. The attaching device of claim 4, wherein the third and fourth straps include holes for accommodating electrodes in a portion extending from the second end towards the first end.

8. The attaching device of claim 4, wherein at least one of the first to fourth straps are made of flexible material.

\* \* \* \* \*